United States Patent
Rinaldi et al.

(10) Patent No.: US 7,276,538 B2
(45) Date of Patent: Oct. 2, 2007

(54) COMPOSITION AND A METHOD FOR TREATING HAIR LOSS

(75) Inventors: Fabio Rinaldi, Milan (IT); Elisabetta Sorbellini, Mediglia (IT); Valter Gatti, Milan (IT); Danila Ingrid Marchioretto, Sesto San Giovanni (IT)

(73) Assignee: Giuliani S.p.A., Milan (IT)

( * ) Notice: Subject to any disclaimer, the term of this patent is extended or adjusted under 35 U.S.C. 154(b) by 0 days.

(21) Appl. No.: 10/502,284

(22) PCT Filed: Jan. 17, 2003

(86) PCT No.: PCT/EP03/00519

§ 371 (c)(1), (2), (4) Date: Jul. 22, 2004

(87) PCT Pub. No.: WO03/063851

PCT Pub. Date: Aug. 7, 2003

(65) Prior Publication Data

US 2005/0147577 A1 Jul. 7, 2005

(30) Foreign Application Priority Data

Feb. 1, 2002 (IT) .......................... MI2002A0189

(51) Int. Cl.
*A61K 31/132* (2006.01)
*A61K 31/13* (2006.01)
*A61K 31/131* (2006.01)

(52) U.S. Cl. ...................... 514/673; 514/579; 514/663; 514/271

(58) Field of Classification Search ...................... None
See application file for complete search history.

(56) References Cited

U.S. PATENT DOCUMENTS 6,331,569 B1 * 12/2001 Kisters et al. .............. 514/561

6,555,140 B1 * 4/2003 Bendera et al. ............. 424/702
2003/0118539 A1 * 6/2003 Fahl et al. ................ 424/70.17

FOREIGN PATENT DOCUMENTS

WO WO96 23490 A 8/1996

OTHER PUBLICATIONS

Dietary supplements market in Italy: Anti-ageing products, OTC News & Market Report, Dec. 1993.*
Rinaldi, et al., Biogenin-based dietary additives. Stimulation of hair shaft growth, Cosmetic Technology, 2002, 5(6), 9-15 (Abstract only).*
H.R. Larsen <http://www.mercola.com/2000/sep/10/milk_cancer.htm>, Sep. 10, 2000, 6 pages; accessed Sep. 1, 2006.*
J. Sanguansermsri and F. Zilliken. Am. J. Clin. Nutr. (1974) 27, pp. 859-865.*
Prof. Oelschlaegel. Original BIOSCALIN report (1986) 3 pages.*
Original Bioscalin. internet document <http://www.permapharm.ch/englisch/englisch/content/o3/home_03.html. accessed Aug. 30, 2006, 2 pages.*
Original Bioscalin history highlights. printed Aug. 30, 2006. 1 page.*
A.S. Koshy and N.R. Vijayalakshmi. Phyto. Res. (2001) 15, pp. 395-400.*
P.I. Hind and M.J. Nancarrow. J. Invest. Dermatol. (1996) 106, pp. 249-253.*
"Which? says hair loss treatments are ineffective." Chemist and Druggist (1999) p. 8. (Proquest Text provided), 1 page.*
Hynd et al., "Inhibition Of Polyamine Synthesis Alters Hair Follicle Function And Fiber Composition," *Journal Of Investigative Dermatology*, 106:249-253 (1996).

* cited by examiner

*Primary Examiner*—Cecilia J. Tsang
*Assistant Examiner*—Andrew D. Kosar
(74) *Attorney, Agent, or Firm*—Nixon Peabody LLP

(57) ABSTRACT

The use of the polyamine known as spermidine, i.e., N-(3-aminopropyl) tetraminethylenediamine, as an active principle in the preparation of a composition for pharmaceutical or dietetic use in man for combating hair loss is disclosed.

6 Claims, 3 Drawing Sheets

COMPOSITION AND A METHOD FOR TREATING HAIR LOSS

CROSS REFERENCE TO RELATED APPLICATIONS

This application is a national stage application under 35 U.S.C. § 371 from PCT Application No. PCT/EP03/00519 filed Jan. 17, 2003, which claims the priority benefit of Italian Application No. MI2002A000189 filed Feb. 1, 2002.

FIELD OF THE INVENTION

The present invention relates to a novel use of the polyamine known as spermidine, i.e. N-(3-aminopropyl) tetramethylenediamine.

BACKGROUND OF THE INVENTION

It is known in the literature that compounds belonging to the class of aliphatic polyamines play a deciding role in controlling the biological mechanisms of growth, division and differentiation of cells and proliferation of animal tissues.

The polyamines in question essentially comprise the compounds putrescine, spermine and spermidine. The latter compound, i.e. N-(3-aminopropyl)tetramethylenediamine, owes its name to the fact that it was first discovered in human sperm. In reality, it is present in virtually all the bodily fluids (blood, saliva, tears and milk). It was subsequently also found in many foods of both animal origin (meat, fish, eggs, milk and cheese) and plant origin (fruit and vegetables). It is of particularly high concentration in human milk (on average about 600 micrograms in milk over 24 hours), where it plays an important role for the newborn. Specifically, in the newborn, the mucosae of the digestive tract are not fully formed and spermidine, taken up with the milk, promotes the growth of the epithelium of the gastric and intestinal mucosa.

Spermidine is therefore an important factor in the growth and proliferation of cells.

SUMMARY OF THE INVENTION

According to the present invention, it has now been found, surprisingly, that a preparation containing spermidine, administered orally to man, results in a stimulation of the hair bulbs with consequent promotion of hair growth, in particular in the case of a pathological hair loss such as that known as telogenic defluvium, characterized by a state of suffering of the hair bulb, leading to an abnormal and excessive loss of hair.

One subject of the present invention is, thus, the use of spermidine as an active principle in the preparation of a composition for pharmaceutical or dietetic use in man to combat pathological hair loss, in particular in the case of telogenic defluvium.

A subject of the present invention is also a composition for pharmaceutical or dietetic use to be administered to man to combat pathological hair loss, characterized in that it comprises spermidine as active principle.

DETAILED DESCRIPTION OF THE INVENTION

Figure 1:
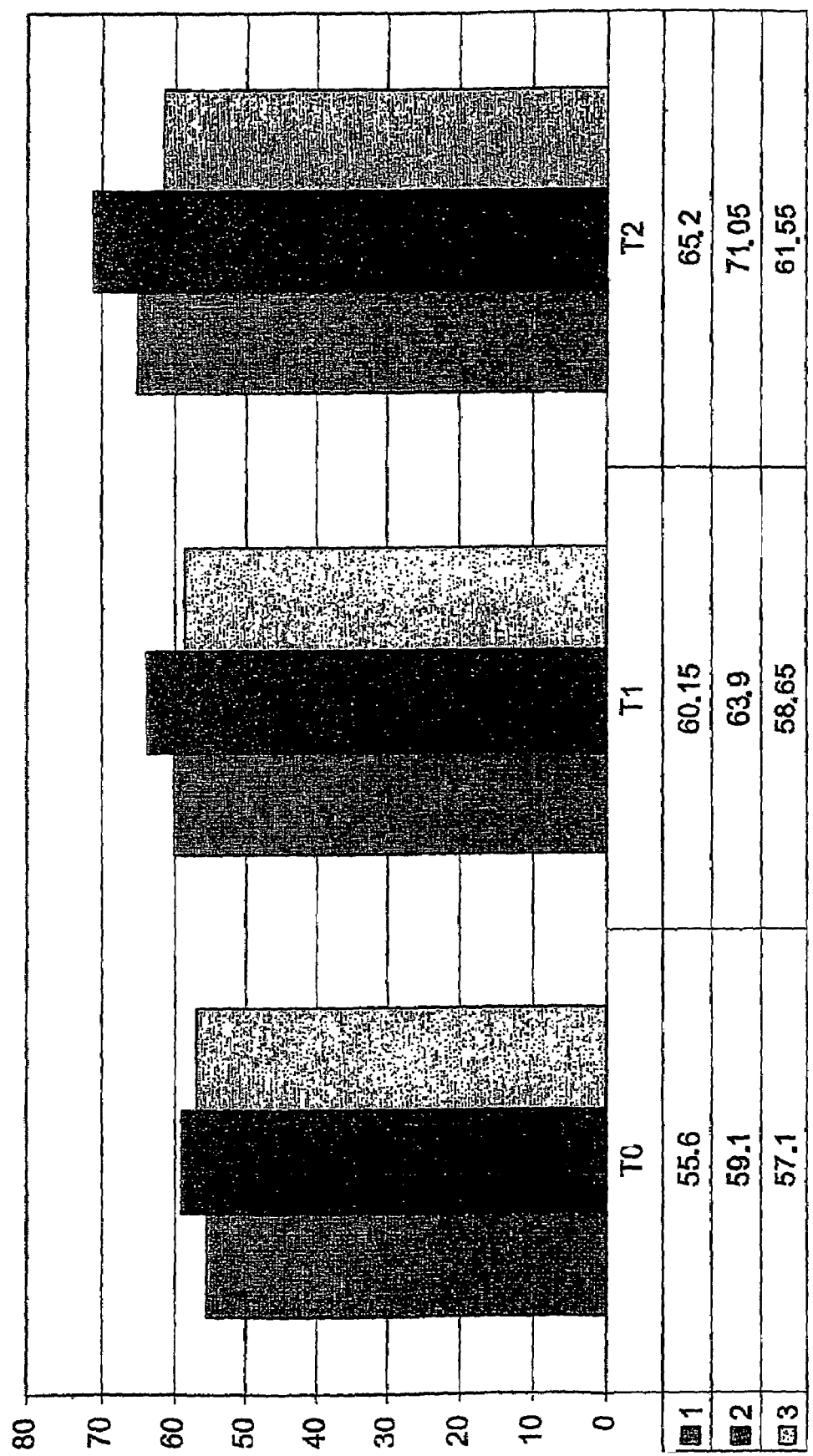
FIG. 1 shows a trichogram of the anagenic phase at times $T_0$, $T_1$, and $T_2$, for the individuals of the three groups.

To understand the characteristics and advantages of the invention more clearly, an experimental study from which they are derived will now be described in greater detail.

To this end, a few fundamental notions regarding the phases of growth of a hair should first be presented. The growth cycle of hair consists essentially of three phases, during which the hair follicle passes from periods of intense growth to periods of quiescence and then of involution. These three phases are: the anagenic phase, i.e. the phase of hair growth, during which there are a number of changes in the dermal papilla in which the cells undergo intense metabolic activity.

The hairs grow 0.3-0.4 mm per day. The hairs are not all in the same growth phase, but rather they alternate. The anagenic phase lasts from 3 to 6 years.

The catagenic phase is the phase of involution lasting from 2 to 3 weeks, during which the hair follicle undergoes profound morphological and metabolic changes. The lower segment is lost, the length of the follicle is reduced by about a third, the bulb decreases in size, the melanocytes stop producing pigment and the papilla becomes atrophic: the hair falls out.

Finally, the telogenic phase is the resting phase, during which the hair follicle is completely inactive. The hair is inside the hair follicle, held by weak intercellular bonds that cause it to stay in the scalp until the start of the new anagenic phase and sometimes even for several successive phases. The telogenic phase lasts from 2 to 4 months.

Every day about 50 hairs die and fall out, and, under normal conditions, are immediately replaced by new members, since the follicles have mutually synchronized life cycles such that the total volume of hairs remains virtually unchanged. In this way, total exchange of the hairs takes place every 2-6 months.

The concept of telogenic defluvium was first introduced by Kligman in 1961. Before that time, it was difficult to distinguish the causes of excessive hair loss (owing to metabolic disturbances, intoxication or infection) from the other more general forms of alopecia.

The diagnosis of telogenic defluvium is made by taking into consideration the growth phases of the hair. When, for various reasons, the anagenic and telogenic phases are altered (and this may take place in both senses: either they are excessively faster or excessively slower than the norm), this results in the phenomenon of telogenic defluvium, which is distinguished by excessive hair loss and by profound morphological alterations in the hair.

The factors that can lead to an imbalance in the hair cycles, with consequent onset of telogenic defluvium, may be: particular physiological conditions (pregnancy), prolonged states of stress and anxiety, use of certain drugs such as, for example, bromocryptine, cimetidine, levodopa, etretinate, lithium, pyridostigmine, propanolol and anti-thyroid drugs, non-balanced diets and deficiencies in vitamins and minerals.

The morphological alterations in the hair during telogenic defluvium may be a microscopically visible destructuring of the shaft, with a consequent reduced mechanical tensile strength and reduced elasticity; alterations in the trichogram; mineral deficiencies, or histological alterations in the hair bulb.

Clinical Study

This controlled, randomized double-blind study was performed according to the present invention by means of the protocols below.

Sixty volunteers of both sexes and ranging between 18 and 60 years old were divided into three groups of 20 individuals each, all having the same level of pathology, i.e. telogenic defluvium existing for at least 2 months.

Some of these individuals were treated for 60 days with one capsule a day of a composition of the invention, according to the following scheme:

Group 1: 20 individuals treated with a composition of the invention containing spermidine alone (0.50 mg per capsule).

Group 2: 20 individuals treated with a composition of the invention according to Example 1 described later (spermidine 0.50 mg per capsule).

Group 3: 20 individuals treated with a placebo, in capsules.

The parameters evaluated were the following:
A) General dermatological visit.
B) Microscopic evaluation of the shaft of the hairs (diameter and possible structural changes in the hair).
C) Trichogram, i.e. evaluation of the bulbs in the anagenic (growth) phase, catagenic (involutive stasis) phase, telogenic (pathological precocious hair loss) phase and exogenic (physiological loss of hairs since they are replaced with new hairs).
D) Haematochemical analysis.
E) Pull test (mechanical tensile strength of the hair).
F) Wash test (count of the hairs lost after washing with shampoo).
G) Possible side effects.

These parameters were evaluated at time $T_0$ (before the start of the treatment); at time $T_1$ (at the end of the 60 days of treatment); and finally at time $T_2$ (30 days after stopping the administration).

Figure 2:
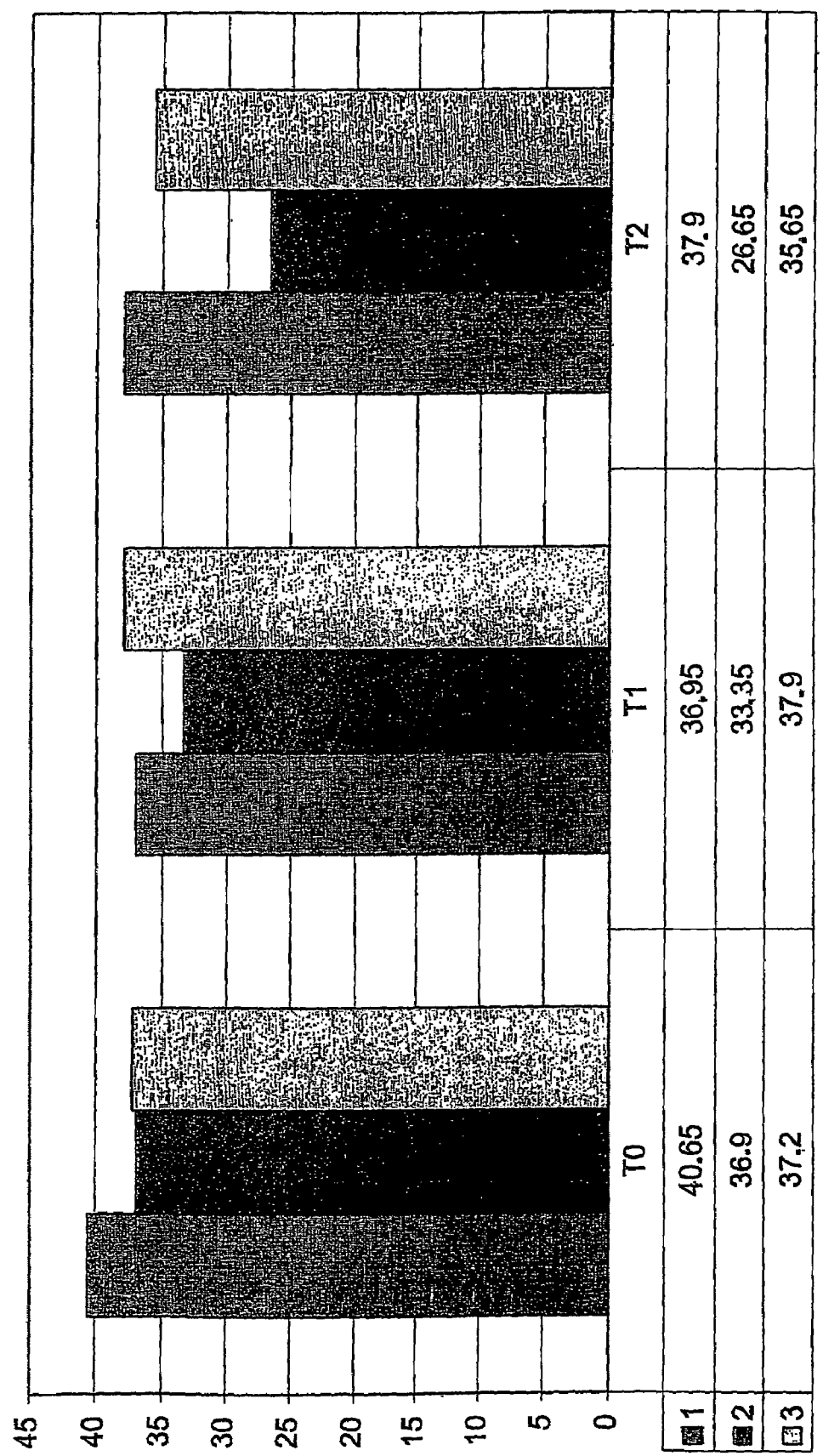
FIG. 2 shows a trichogram of the telogenic phase at times $T_0$, $T_1$, and $T_2$, for the individuals of the three groups.

The results were as follows:
A) The dermatological visit revealed an appreciable and significant reduction in the hair loss and an improvement in the structure of the shaft in the groups of patients 1 and 2 compared with the placebo group 3.
B) Microscopic evaluation of the shaft The diameter of the hair shaft increases quite substantially in groups 1 and 2, whereas it remains virtually unchanged in the placebo group 3.
C) The trichogram is the parameter that, together with the wash test, gave the most interesting results. In this regard, reference is made to the diagrams of FIGS. 1 and 2 in the attached drawings. These show the trichogram of the anagenic and telogenic phases at times $T_0$ (before the start of the treatment); at time $T_1$ (at the end of the 60 days of treatment); and finally at time $T_2$ (30 days after stopping the administration) for the individuals of the three groups, 1 (grey column), 2 (black column) and 3 (pale column). The percentage of hairs in the anagenic phase (FIG. 1) and in the telogenic phase (FIG. 2) for the treated individuals belonging to the three groups under consideration is shown on the y-axis, and the said times T are shown on the x-axis, under which are tabulated the said percentages found.

Specifically, the microscopic analysis of the state of the bulb reveals that the number of bulbs in the anagenic phase increases significantly in Groups 1 and 2 and, in parallel, in the same Groups, the telogenic phase decreases significantly. In contrast, in the placebo group 3, the anagenic and telogenic phases are not significantly changed.

In particular, a 17.2% increase in the anagenic phase at $T_2$ relative to $T_0$ (with an 8.1% increase at $T_1$) was found in Group 1.

A 20.2% increase in the anagenic phase at $T_2$ relative to $T_0$ (with an 8.12% increase at $T_1$) was found in Group 2.

A 7.79% increase in the anagenic phase at $T_2$ relative to $T_0$ (with a 2.7% increase at $T_1$) was found in Group 3. The change of about 7.79% in the anagenic phase from $T_0$ to $T_2$ in the placebo group is comparable to the cyclic changes that take place within the hair bulbs.

In parallel, the telogenic phase decreased by:
6.76% at $T_2$ (9.1% at $T_1$) in Group 1
27.7% at $T_2$ (9.6% at $T_1$) in Group 2
4.16% at $T_2$ in Group 3, for which, however, an increase in the telogenic phase (of about 1.88%) is actually found at $T_1$.

D) The haematochemical analyses gave values within the norm for all the Groups 1, 2 and 3.
E) Pull test:

The mechanical tensile strength of the hair increased significantly in Groups 1 and 2, whereas it remained virtually unchanged in the placebo Group 3.

F) Wash test. This test makes it possible not only to quantify the number of hairs lost after shampooing, but also, by means of a suitable microscopic analysis, to evaluate the phase of the cycle in which the bulb was found when the hair fell out: pathological loss (telogenic) or phase of physiological exchange (exogenic).

Figure 3:
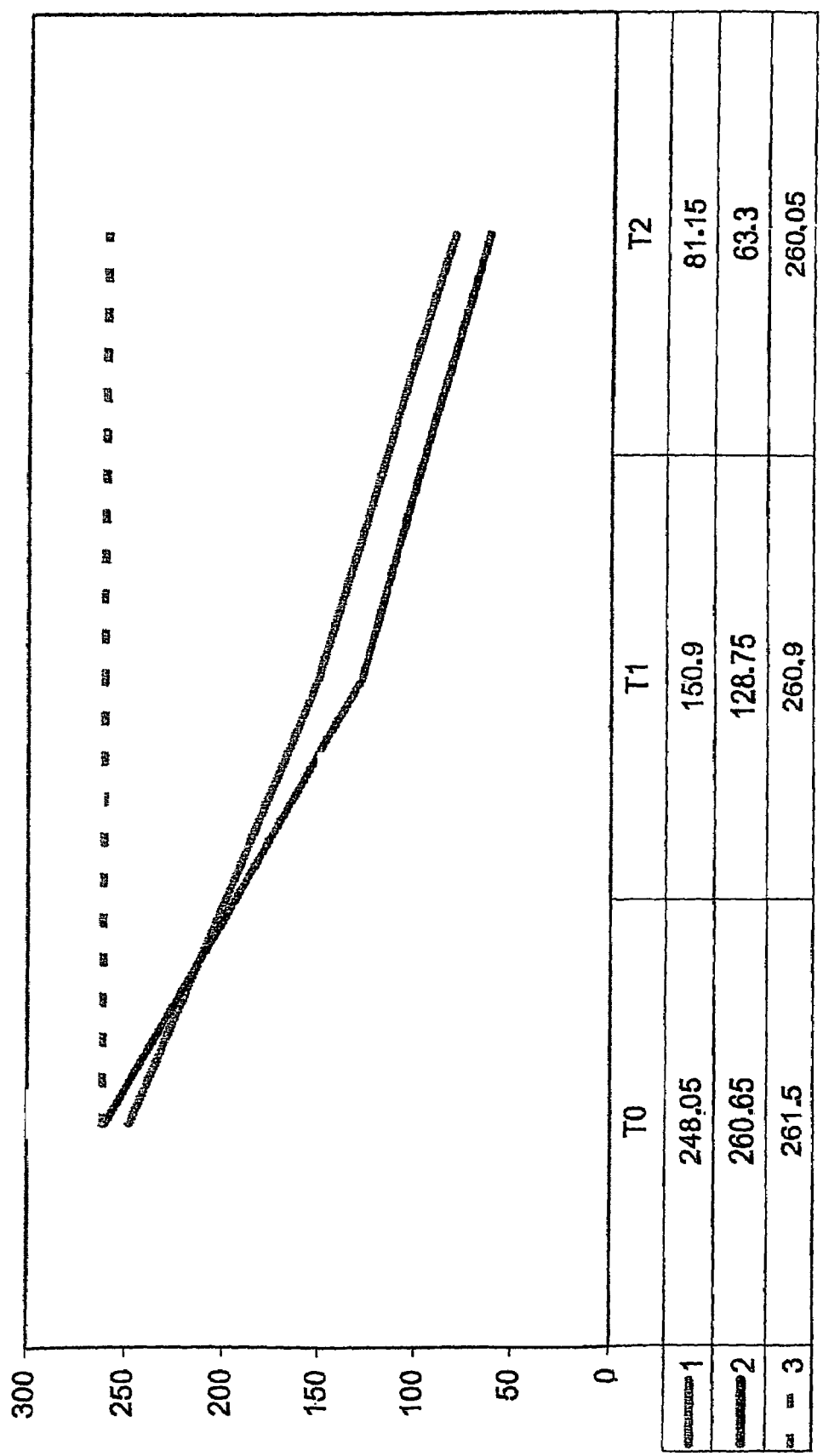
FIG. 3 is a graphic representation of the results of the wash test.

The test results are given in the graph of FIG. 3 in the attached drawings. In this graph, the number of hairs lost during washing for the individuals of the three groups mentioned above is given on the y-axis, and the said times T [$T_0$ (before starting the treatment); $T_1$ (at the end of the 60 days of treatment); $T_2$ (30 days after stopping the administration)] are given on the x-axis, under which are tabulated the values found.

As may be seen, the number of hairs lost in the wash test decreases significantly for the treatment process in Groups 1 and 2 (solid lines), whereas it remains unchanged in the placebo Group 3 (dashed line in the graph).

In addition, by analysing the bulbs of the lost hairs, the following important observation was made. In Group 3 treated with placebo, more than 90% of the lost hairs were in the telogenic phase (pathological loss) and only 3% were in the exogenic phase (physiological loss).

In Groups 1 and 2 this ratio changes, since the hairs in the exogenic phase are 33% in Group 1 and 46% in Group 2, with a consequent reduction in the hairs in the telogenic phase, which was found to be 63% in Group 1 and 52% in Group 2.

Thus, in Groups 1 and 2, among the lost hairs, there was a significant decrease in the percentage of hairs in the telogenic phase (pathological loss) and a proportionate increase in the percentage of hairs in the exogenic phase (physiological loss by exchange).

G) The side effects were mild and all disappeared as the treatment continued, taking care to take the capsule during the main meal, at $T_1$.

According to the present invention, it was thus experimentally found that the oral administration to man of a composition containing spermidine, preferably combined with other components such as methionine, bioflavonoids, vitamins and mineral salts, is capable of slowing down and stopping excessive hair loss in the case of telogenic defluvium, and simultaneously of improving the strength and general health of the hair.

The pull test demonstrated that spermidine, either in unmodified form or combined with other micro-nutrients, increases the mechanical tensile strength of the hair.

The trichogram and the wash test made it possible to demonstrate large variations arising in the hair bulb following treatments with spermidine in unmodified form or combined with other active components. Not only is the number of hairs lost after washing substantially reduced, but also, among those lost, the number in the telogenic phase (pathological loss) is substantially decreased when compared with the number in the exogenic phase (loss by physiological exchange). Thus, the treatment with spermidine in unmodified form or with spermidine combined with other micronutrients has substantially modified the cycle of the hair altered by the telogenic defluvium pathology, returning it to the normal values of physiological exchange.

For the use of spermidine according to the present invention, it is convenient to formulate it in compositions preferably for oral use, and preferably as a dietetic product. It may also be formulated in compositions for topical use on the scalp.

A number of examples, not intended to be limiting, of compositions according to the invention will now be described.

EXAMPLE 1

Dietetic Composition for Making the Hair Robust and Reducing Hair Loss

| Sealed rigid plant capsules Each capsule contains: | |
|---|---|
| Active principles | |
| Methionine | 300.00 mg |
| Vitamin C | 90.00 mg |
| Polyphenols from *Vitis vinifera* | 5.00 mg |
| Vitamin E | 15.00 mg |
| Calcium pantothenate | 9.00 mg |
| Zinc (as amino acid chelate) | 7.50 mg |
| Vitamin $B_6$ | 2.00 mg |
| Copper (as amino acid chelate) | 1.25 mg |
| Spermidine | 0.50 mg |
| Folic acid | 0.15 mg |
| Biotin | 0.05 mg |
| Excipients | |
| Hydroxypropylmethylcellulose | 110.00 mg |
| Talc | 21.00 mg |
| Magnesium stearate | 6.50 mg |
| Colloidal silica | 2.85 mg |
| Natural colorants | 2.50 mg |

EXAMPLE 2

Dietetic Composition for Making the Hair Robust and Reducing Hair Loss

| Packets to be dissolved in water Each packet contains: | |
|---|---|
| Active principles | |
| Methionine | 300.00 mg |
| Vitamin C | 90.00 mg |
| Polyphenols from *Vitis vinifera* | 20.00 mg |
| Vitamin E | 15.00 mg |
| Calcium pantothenate | 9.00 mg |
| Zinc (as amino acid chelate) | 7.50 mg |
| Beta-carotene | 4.20 mg |
| Vitamin $B_6$ | 2.00 mg |
| Copper (as amino acid chelate) | 1.25 mg |
| Spermidine | 0.50 mg |
| Folic acid | 0.30 mg |
| Biotin | 0.15 mg |
| Excipients | |
| Maltodextrin | 2000.00 mg |
| Sodium citrate | 350.00 mg |
| Citric acid monohydrate | 200.00 mg |
| Flavourings | 160.00 mg |
| Colloidal silica | 65.00 mg |
| Aspartame | 30.00 mg |
| Acesulfame K | 7.00 mg |
| Natural colorants | 3.50 mg |

EXAMPLE 3

Cosmetic Attack Lotion (initial treatment) for Making the Hair Robust and Reducing Hair Loss

| In ampules Each ampule of 10 ml of solution contains: | |
|---|---|
| Active principles | |
| Spermidine | 2 mg |
| Catechin and quercetin complex | 40 mg |
| Methylsulphonylmethane | 400 mg |
| Azeoglycine (potassium azeloyl diglycinate) | 300 mg |
| Sunflower oil and rosemary oil | 5 mg |
| Menthyl lactate | 25 mg |
| Calcium pantothenate | 16 mg |
| Biotin | 0.15 mg |
| Excipients | |
| Ethyl alcohol | 4.0 ml |
| Fragrance | 5.0 mg |
| Natural colorants | 0.2 mg |
| Purified water | qs 10 ml |

EXAMPLE 4

Cosmetic Maintenance Lotion (continuation of treatment) for Making the Hair Robust and Reducing Hair Loss

| In bottles 100 ml of solution contain: | |
|---|---|
| Active principles | |
| Spermidine | 5 mg |
| Catechin and quercetin complex | 200 mg |
| Methylsulphonylmethane | 2000 mg |
| Azeoglycine (potassium azeloyl diglycinate) | 3000 mg |
| Sunflower oil and rosemary oil | 50 mg |

-continued

| In bottles 100 ml of solution contain: | |
|---|---|
| Menthyl lactate | 250 mg |
| Calcium pantothenate | 80 mg |
| Biotin | 1.5 mg |
| Excipients | |
| Ethyl alcohol | 35 ml |
| Natural colorants | 900 mg |
| Fragrance | 50 mg |
| Purified water | qs 100 ml |

EXAMPLE 5

Cosmetic Balm for Making the Hair Robust and Reducing Hair Loss

| In bottles 100 ml of balm contain: | |
|---|---|
| Active principles | |
| Spermidine | 10 mg |
| Catechin and quercetin complex | 400 mg |
| Methylsulphonylmethane | 4000 mg |
| Azeoglycine (potassium azeloyl diglycinate) | 3000 mg |
| Sunflower oil and rosemary oil | 50 mg |
| Menthyl lactate | 250 mg |
| Calcium pantothenate | 80 mg |
| Biotin | 1.5 mg |
| Excipients | |
| Cetearyl alcohol | 5000 mg |
| PEG-15 cocopolyamine | 5000 mg |
| Oat protein hydrolysate | 3000 mg |
| Glycerol | 3000 mg |
| Cetyl alcohol | 2000 mg |
| Quaternium-52 | 1000 mg |
| Phenoxyethanol | 300 mg |
| Methyl-ethyl-propyl para-oxybenzoates | 200 mg |
| Fragrance | 500 mg |
| Colorants | 1000 mg |
| Purified water | qs 100 ml |

The invention claimed is:

1. A method for treating hair loss resulting from telogenic defluvium comprising administering to a human having the pathology known as telogenic defluvium a pharmaceutical or dietetic composition comprising spermidine as an active principle to treat hair loss.

2. The method according to claim 1, wherein following administration the telogenic phase in the growth cycle of the hair is reduced.

3. The method according to claim 1, wherein following administration the hair is improved in strength and general health.

4. A method for treating hair loss resulting from telogenic defluvium comprising administering to a human having the pathology known as telogenic defluvium a pharmaceutical or dietetic composition comprising spermidine as an active principle to treat hair loss, wherein the composition further comprises methionine, vitamin C, polyphenols, vitamin E, calcium pantothenate, zinc (as amino acid chelate), vitamin $B_6$, copper (as amino acid chelate), folic acid and biotin.

5. The method according to claim 4, wherein the composition comprises:

| | |
|---|---|
| Methionine | 300.00 mg |
| Vitamin C | 90.00 mg |
| Polyphenols from *Vitis vinifera* | 5.00 mg |
| Vitamin E | 15.00 mg |
| Calcium pantothenate | 9.00 mg |
| Zinc (as amino acid chelate) | 7.50 mg |
| Vitamin $B_6$ | 2.00 mg |
| Copper (as amino acid chelate) | 1.25 mg |
| Spermidine | 0.50 mg |
| Folic acid | 0.15 mg |
| Biotin | 0.05 mg. |

6. A method for treating hair loss resulting from telogenic defluvium comprising administering to a human having the pathology known as telogenic defluvium a pharmaceutical or dietetic composition to treat hair loss, wherein the composition to be administered to man to treat hair loss is formulated for oral administration and comprises an oral vehicle and spermidine.

* * * * *